US008435520B2

(12) United States Patent
Schuurman et al.

(10) Patent No.: US 8,435,520 B2
(45) Date of Patent: May 7, 2013

(54) COMBINATIONS OF IMMUNOSUPPRESSIVE AGENTS FOR THE TREATMENT OR PREVENTION OF GRAFT REJECTIONS

(75) Inventors: Hendrik J. Schuurman, Charlestown, MA (US); Emanuele Luigi Maria Cozzi, Padua (IT); Francoise Richard, St. Louis (FR); Guy Taccard, Hegenheim (FR); David James Graham White, Cambridge (GB); Peter John Friend, Oxford (GB); John Wallwork, Cambridge (GB); Paolo Brenner, Neuried (DE)

(73) Assignee: Paolo Brenner, Neuried (DE)

( * ) Notice: Subject to any disclaimer, the term of this patent is extended or adjusted under 35 U.S.C. 154(b) by 0 days.

(21) Appl. No.: 13/025,347

(22) Filed: Feb. 11, 2011

(65) Prior Publication Data
US 2011/0142953 A1 Jun. 16, 2011

Related U.S. Application Data

(63) Continuation of application No. 12/109,210, filed on Apr. 24, 2008, now abandoned, which is a continuation of application No. 11/599,814, filed on Nov. 15, 2006, now abandoned, which is a continuation of application No. 11/178,573, filed on Jul. 11, 2005, now abandoned, which is a continuation of application No. 10/035,663, filed on Nov. 7, 2001, now abandoned, which is a continuation of application No. PCT/EP00/04250, filed on May 10, 2000.

(30) Foreign Application Priority Data

May 10, 1999 (GB) .................................. 9910835.9
Oct. 27, 1999 (GB) .................................. 9925443.5

(51) Int. Cl.
*A61K 39/395* (2006.01)
*A61K 38/13* (2006.01)
*A61K 47/26* (2006.01)
*A61K 47/00* (2006.01)

(52) U.S. Cl.
USPC .... 424/140.1; 424/93.2; 424/810; 424/278.1; 800/17; 514/20.5; 435/1.1

(58) Field of Classification Search .................. None
See application file for complete search history.

(56) References Cited

U.S. PATENT DOCUMENTS

| 5,593,677 | A | 1/1997 | Reichert et al. | 424/154.1 |
|---|---|---|---|---|
| 5,631,282 | A | 5/1997 | Goetz | 514/450 |
| 5,651,968 | A | 7/1997 | Good et al. | 424/140.1 |
| 5,665,728 | A | 9/1997 | Morris et al. | 514/291 |
| 5,688,824 | A | 11/1997 | Williams | 514/378 |
| 5,843,452 | A | 12/1998 | Wiedmann et al. | 424/759 |
| 5,962,415 | A | 10/1999 | Nadler | 514/12 |
| 6,825,395 | B1 | 11/2004 | Murakami et al. | 800/14 |

FOREIGN PATENT DOCUMENTS

| WO | 92/00739 | 1/1992 |
|---|---|---|
| WO | 93/03735 | 3/1993 |
| WO | 97/35575 | 10/1997 |
| WO | 97/38689 | 10/1997 |
| WO | 98/04279 | 2/1998 |
| WO | 98/11894 | 3/1998 |
| WO | 99/03336 | 1/1999 |

OTHER PUBLICATIONS

Buhler et al., "Xenotransplantation—State of the Art—Update 1999", Frontiers in Bioscience, vol. 4, pp. d416-d432 (1999).
Fujino et al., "Evaluation of Cyclosporine, Mycophenolate Mofetil, and Brequinar Sodium Combination Therapy on Hamster-to-Rat Cardiac Xenotransplantation", Transplantation, vol. 57, No. 1, pp. 41-46 (1994).
Halloran et al., "Molecular Mechanisms of New Immunosuppressants", Clin. Transplantation, vol. 10, pp. 118-123 (1996).
Hulett et al., Prolongation of Allograft and Xenograft Survival With Mycophenolate Mofetil (RS-61443) and Brequinar Sodium (DUP-785), Transplant Proceedings, vol. 25, No. 1, pp. 700-701 (1993).
Schuurman et al., "SDZ RAD, A New Rapamycin Derivative", Transplantation, vol. 64, No. 1, pp. 32-35 (1997).
Tu et al., "The Synergistic Effects of Cyclosporine, Sirolimus, and Brequinar on Heart Allograft Survival in Mice", Transplantation, vol. 59, No. 2, pp. 177-189 (1995).
Waterworth et al., "Life-Supporting Pig-to-Baboon Heart Xenotransplantation", J. Heart and Lung Transplant., vol. 17, No. 12, pp. 1201-1207 (1998).
Wennberg et al., "Immunosuppression With Cyclosporin A in Combination with Leflunomide and Mycophenolate Mofetil Prevents Rejection of Pig-Islets Transplanted into Rats", Transplant. Proceedings, vol. 28, No. 2, p. 819 (1996).
DermNet NZ, http:dermnetnz.org/treatment/mycophenolate.html, Mar. 6, 2005.
Hasan et al., Transplantation, vol. 54, pp. 408-413, (1992).
Kahan et al., Immunol. Rev., vol. 136, pp. 29-49, (1993).
Tueveson et al., Immun. Rev., vol. 136, pp. 99-109, (1993).
Adachi et al., Transplantation Proc., vol. XIX, pp. 1145-1148, (1987).
P. Brenner et al., Effects of Prolonged Cold Stroage Time in Xenotransplantation (J. Heart Lung Transplant), 1999, 1211-1217, vol. 18, No. 12.

(Continued)

*Primary Examiner* — Ronald Schwadron
(74) *Attorney, Agent, or Firm* — Kilyk & Bowersox, P.L.L.C.

(57) ABSTRACT

A pharmaceutical composition useful in the treatment or prevention of transgenic xenograft rejection comprising immunosuppressant compounds selected from the group consisting of an IL-2 transcription inhibitor and immunosuppressant compounds that immunosuppress for B-cell-mediated or antibody-mediated rejection of xenografts, and pharmaceutically acceptable diluents or carriers, and a method of preventing hyperacute rejection, reducing early graft damage, improving early xenograft function and promoting long term survival of said transgenic xenografts comprising the steps of i) contacting the body fluid removed from a human recipient with a xenoantigenic material which is bound to a biocompatible solid support, ii) reintroducing the treated body fluid into the recipient, and iii) treating the recipient with said pharmaceutical composition.

20 Claims, No Drawings

OTHER PUBLICATIONS

P. Brenner et al., Combination of hDAF-Transgenic Pig Hearts and Immunoadsorption in Heterotopic Xenotransplantation of Immunosuppressed Baboons (Transplantation Proceedings), 2005, 483-486, vol. 37.

P. Brenner et al., Mean Xenograft Survival of 14.6 Days in a Small Group of hDAF-Transgenic Pig Hearts Transplanted Orthotopically Into Baboons (Transplantation Proceedings), 2005, 472-476, vol. 37.

P. Brenner et al., The Influence of antibody and complement removal with a Ig-Therasorb column in a xenogeneic working heart model (European Journal of Cardio-thoracic Surgery), 1999, 672-679, vol. 15.

G. Byrne et al., Identification of New Carbohydrate and Membrane Protein Antigens in Cardiac Xenotransplantation (Transplantation), 2011, 287-292, vol. 91.

D. K. C. Cooper et al., Report of the Xenotransplantation Advisory Committee of the International Society for Heart and Lung Transplantation: The Present Status of Xenotransplantation and Its Potential Role in the Treatment of End-Stage Cardiac and Pulmonary Diseases (J. Heart Lung Transplant), 2000, 1125-1165, vol. 19, No. 12.

A. Bauer et al., hDAF porcine cardiac xenograft maintains cardiac output after orthotopic transplantation into baboon—a perioperative study (Xenotransplantation), 2005, 444-449, vol. 12.

A. Bauer et al., First experience with heterotopic thoracic pig-to-baboon cardiac xenotransplantation (Xenotransplantation), 2010, 243-249, vol. 17.

U. Brandl, Transgenic Animals in Experimental Xenotansplantation Models: Orthotopic Heart Transplantation in the Pig-to-Baboon Model (Transplantation Proceedings), 2007, 577-578, vol. 39.

Burcin Ekser et al., Overcoming the barriers to xenotransplantation: prospects for the future (Expert Rev. Clin. Immunol.), 2010, 219-230, vol. 6, No. 2.

Burcin Ekser et al., Xenotransplantation of solid organs in the pig-to-primate model (Transplant Immunology), 2009, 87-92, vol. 21.

C. Hammer, Evolution: Its Complexity and Impact on Xenotransplantation (Xenotransplantation), 1997, 716-735, Cooper et al. (Editors), Springer:Heidelberg.

Shu S. Lin et al., The role of natural anti-Gal$\alpha$1-3Gal antibodies in hyperacute rejection of pig-to-baboon cardiac xenotransplants (Transplant Immunology), 1997, 212-218, vol. 5.

Christopher G. A. McGregor et al., Cardiac xenotransplantation: Recent Preclinical progress with 3-month median survival (The Journal of Thoracic and Cardiovascular Surgery), 2005, 844-851, vol. 130.

Steffen Pfeiffer et al., Hyperacute Lung Rejection in the Pig-to-Human Model 4: Evidence for Complement and Antibody Independent Mechanisms (Transplantation), 2005, 662-671, vol. 79, No. 6.

Emanuele Cozzi, Maintenance triple immunosuppression with cyclosporin A, mycophenolate sodium and steroids allows prolonged survival of primate recipients of hDAF porcine renal xenografts (Xenotransplantation), 2003, 300-310, vol. 10.

T. Kozlowski et al., Depletion of anti-Gal(alpha)1-3Gal antibody in baboons by specific alpha-Gal immunoaffinity columns. (Xenotransplantation), May 1998, 122-31, vol. 5, No. 2 (Abstract).

S. Taniguchi, In vivo immunoadsorption of antipig antibodies in baboons using a specific Gal(alpha)1-3Gal column. (Transplantation), Nov. 1996, 1379-1384, vol. 62, No. 10 (Abstract).

Carol J. Phelps et al., Production of $\alpha$1,3-Galactosyltransferase-Deficient Pigs (Science), Jan. 2003, 411-414, vol. 299.

Richard N. Pierson III et al., Current status of xenotransplantation and prospects for clinical application (Xenotransplantation), 2009, 263-280, vol. 16.

Rafael Manez, Failure to delete anti-Gal$\alpha$1-3Gal antibodies after pig-to-baboon organ xenotransplantation by immunoaffinity columns containing multiple Gal$\alpha$l-3Gal oligosaccharides (Xenotransplantation) 2004, 408-415, vol. 11.

S. Taniguchi, In vivo immunoadsorption of antipig antibodies in baboons using a specific Gal(alpha)1-3Gal column. (Transplantation), Nov. 1996, 1379-1384, vol. 62, No. 10.

COMBINATIONS OF IMMUNOSUPPRESSIVE AGENTS FOR THE TREATMENT OR PREVENTION OF GRAFT REJECTIONS

This is a continuation of U.S. patent application Ser. No. 12/109,210, filed Apr. 24, 2008, now abandoned, which is a continuation of U.S. patent application Ser. No. 11/599,814 filed Nov. 15, 2006, now abandoned, which is a continuation of U.S. patent application Ser. No. 11/178,573, filed Jul. 11, 2005, now abandoned, which is a continuation of U.S. patent application Ser. No. 10/035,663, filed Nov. 7, 2001, now abandoned, which is a continuation of International Application No. PCT/EP00/004250 filed May 10, 2000, which claims priority to United Kingdom Patent Application No. 9910835.9, filed May 10, 1999, and United Kingdom Patent Application No. 9925443.5, filed Oct. 27, 1999, the contents of all of which are incorporated herein by reference in their entireties.

This is a continuation of International Application No. PCT/EP00/04250, filed May 10, 2000, the contents of which are incorporated herein by reference.

This invention is concerned with certain novel pharmaceutical compositions comprising combinations of immunosuppressive agents, the use of such compositions for the treatment or prevention of xenograft rejection, and novel therapies for facilitating transplantation of xenogenic tissues or organs into humans and to promote long term survival of said tissues or organs.

In order for xenotransplantation to present a clinically viable treatment for organ disease, it is necessary to effectively treat or prevent acute rejection and chronic rejection of donor organs. Effective treatments need to inhibit T-cells, and also B-cell-mediated or antibody-mediated rejection.

However, a problem associated with combining compounds that suppress T-cells as well as compounds that act against B-cell-mediated rejection or antibody-mediated rejection is the potential and unpredictable pharmacokinetic interaction of the compounds which may influence the toxicity or the immunosuppression of the combination.

Surprisingly, the applicant has found that pharmaceutical compositions comprising a certain combination of immunosuppressant compounds display good tolerability whilst at the same time display prolonged xenograft survival of donor organs, few rejection episodes and good graft function.

The invention provides in one aspect a method of treatment or prevention of xenograft rejection which comprises administering of at least two immunosuppressant compounds independently selected from the group consisting of (a) IL-2 transcription inhibitors and (b) immunosuppressant compounds that immunosuppress for B-cell-mediated or antibody-mediated rejection of xenografts.

Pharmaceutical compositions useful in the treatment or prevention of xenograft rejection comprise at least two immunosuppressant compounds selected from the group consisting of (a) IL-2 transcription inhibitors and (b) immunosuppressant compounds that immuno-suppress for B-cell-mediated or antibody-mediated rejection of xenografts.

Therefore, the invention provides in another aspect a pharmaceutical composition useful in the prevention or treatment of xenograft rejection comprising combinations of immunosuppressant compounds selected from the group consisting of (a) IL-2 transcription inhibitors and (b) immunosuppressant compounds that immunosuppress for B-cell-mediated or antibody-mediated rejection of xenografts.

In another aspect, the group of immunosuppressant compounds consists of (a) an IL-2 transcription inhibitor and (b) immunosuppressant compounds that immunosuppress for B-cell-mediated or antibody-mediated rejection of xenografts.

As used herein, including the claims, the combinations of immunosuppressant agents cover the administration of the agents for simultaneous, separate or sequential use. Thus e.g. they may be in a package or in a blister.

The term "IL-2 transcription inhibitor" refers to immunosuppressive compounds whose immunosuppressive activity derives principally or in significant part from their direct or indirect inhibition of IL-2 gene transcription, e.g. corticosteroids, ascomycins and cyclosporines, FK506 and their various derivatives and analogues.

Cyclosporine, (also known as cyclosporin A or cyclosporin) is an immunosuppressive cyclic undecapeptide. Its structure is disclosed, e.g. in the Merck Index, 11th edition; Merck & Co. Inc., Rahway, N.J., USA (1989) under listing 2759. Formulations of cyclosporine are commercially available under the trademark SANDIMMUN or SANDIMMUNE and a microemulsion preconcentrate formulation of cyclosporine is sold under the trademark NEORAL or OPTORAL.

Immunosuppressant compounds that immunosuppress for B-cell-mediated or antibody-mediated rejection of xenografts include rapamycin and/or derivatives thereof including 40-O-(2-hydroxyethyl)-rapamycin, or myriocin analogues such as 2-amino-2-(2-[4-octylphenyl)-ethyl]-1,3-propanediol, or mycophenolic acid (MPA) or pharmaceutically acceptable salts thereof, or cyclophosphamide.

A preferred rapamycin derivative is 40-O-(2-hydroxyethyl)-rapamycin. 40-O-(2-hydroxyethyl)-rapamycin is a rapamycin derivative the structure of which is disclosed in WO 94/09010, example 8, and is a semi-synthetic derivative of rapamycin. The structure of rapamycin is given in Kesseler, H., et al.; 1993; Helv. Chim. Acta; 76; 117, and numerous immunosuppressive derivatives and analogues of rapamycin are known.

MPA sodium salt is known and is disclosed in published patent application No. WO 97/38689. Even more preferred is a MPA sodium salt in form of a formulation as described in U.S. Pat. No. 6,025,391 which is incorporated herein by reference.

More preferred pharmaceutical compositions according to the invention comprise combinations of a pharmaceutically acceptable salt of mycophenolic acid (MPA), for example the sodium salt of MPA, rapamycin and/or derivatives thereof including 40-O-(2-hydroxy-ethyl)-rapamycin, and IL-2 transcription inhibitors.

Most preferred pharmaceutical compositions according to the invention comprise double combinations of MPA sodium salt and cyclosporine or 40-O-(2-hydroxyethyl)-rapamycin, the double combination of cyclosporine and 40-O-(2-hydroxyethyl)-rapamycin, or a triple combination of MPA sodium salt, cyclosporine and 40-O-(2-hydroxyethyl)-rapamycin.

Pharmaceutical compositions according to the invention act synergistically, i.e. the immuno-suppressive effect of the combination of compounds is greater than additive. This has the advantage that relatively low doses of each compound may be used in the pharmaceutical compositions. Synergy may be calculated according to a method described in Berenbaum, Clin. Exp. Immunol. (1977) 28:1.

The indications for which the pharmaceutical compositions are useful are conditions associated with, or causal to, transplant rejection, for example treatment (including amelioration, reduction, elimination or cure of etiology or symptoms) or prevention (including substantial or complete restriction, prophylaxis or avoidance) of xenograft rejection, including acute and chronic rejection of an organ when the organ donor is of a different species from the recipient, most especially rejection mediated by B-cells or antibody-mediated rejection.

Preferably, in one group of embodiments there is no IL-2 transcription inhibitor present. In another group of embodiments, one IL-2 transcription inhibitor is present, and yet in another group of embodiments, two or more IL-2 transcription inhibitors are present.

More particularly the method comprises the administration of a pharmaceutical composition comprising a combination of a pharmaceutically acceptable salt of MPA, for example the sodium salt of MPA, rapamycin and/or derivatives thereof including 40-O-(2-hydroxyethyl)-rapamycin, and IL-2 transcription inhibitors.

Preferably the method comprises the administration of a pharmaceutical composition comprising a combination of MPA sodium salt and one or more immunosuppressant compounds selected from the group consisting of (a) an IL-2 transcription inhibitor, especially cyclosporine, and (b) rapamycin and/or derivatives thereof, especially 40-O-(2-hydroxyethyl)-rapamycin.

In a further aspect of the invention there is provided the use of a pharmaceutical composition comprising compounds selected from the group consisting of (a) an IL-2 transcription inhibitor and (b) immunosuppressant compounds that immunosuppress for B-cell-mediated or antibody-mediated rejection of xenografts, in the treatment of a condition as hereinabove described.

More particularly the invention provides the use of a pharmaceutical composition comprising a combination of a pharmaceutically acceptable salt of MPA, for example the sodium salt of MPA, rapamycin and/or derivatives thereof including 40-O-(2-hydroxyethyl)-rapamycin, and IL-2 transcription inhibitors, in the treatment of a condition as hereinabove described.

Preferably the invention provides the use of pharmaceutical compositions comprising combinations of MPA sodium salt and one or more immunosuppressant compounds selected from the group consisting of (a) an IL-2 transcription inhibitor, especially cyclosporine, and (b) rapamycin and/or derivatives thereof, especially 40-O-(2-hydroxyethyl)-rapamycin, in the treatment of a condition as hereinabove described.

In yet another aspect of the invention there is provided a kit-of-parts comprising any of the pharmaceutical compositions hereinabove described, especially a pharmaceutical composition comprising MPA sodium salt and one or more immunosuppressant compounds selected from the group consisting of (a) an IL-2 transcription inhibitor, especially cyclosporine, and (b) rapamycin and/or derivatives thereof, especially 40-O-(2-hydroxyethyl)-rapamycin, together with instructions for use in the treatment or prevention of a condition as hereinabove described.

The dosages of the compounds will vary depending on the individual to be treated, the route of administration and the nature and severity of the condition to be treated. For example, in the prevention or treatment of xenograft rejection, an initial dose of about 2 to 3 times the maintenance dose may suitably be administered about 4 to 12 hours before transplantation, followed by a daily dosage of 2 to 3 times the maintenance dosage for one to two weeks, before gradually tapering down the dose at a rate of about 5% per week to reach the maintenance dose.

The exact dosage of each compound may be determined having regard to the particular therapeutic blood levels required for each compound. Thus, through judicious selection of the dosage of each compound, surprisingly it has been found that pharmaceutical compositions may be formed that are tolerated and which display synergistic action in immune suppression.

Accordingly, in another aspect of the invention there is provided a pharmaceutical composition comprising (a) an IL-2 transcription inhibitor, in particular cyclosporine, that may be delivered to a patient at a dosage such that the 16 hour blood trough level is e.g. up to 1500 ng per ml, e.g. 50 to 1500, e.g. 50 to 1000 ng per ml, e.g. up to 500 ng per ml, e.g. 50 to 500 ng per ml, more particularly 100 to 500 ng per ml, e.g. 300 to 500 ng per ml, and (b) an immunosuppressant compound that immunosuppresses for B-cell-mediated or antibody-mediated rejection of xenografts that may be delivered to a patient at a dosage such that the 16 hour blood trough level is e.g. 0.1 to 20, e.g. 0.1 to 10, e.g. 1 to 10, preferably 3 to 6 µg per ml of the active substance, or is e.g. 1 to 90, e.g. 5 to 50, e.g. 10 to 35 ng per ml, more particularly 10 to 20 ng per ml.

In particularly preferred pharmaceutical compositions, a pharmaceutically acceptable salt of MPA, for example the sodium salt of MPA, may be delivered to a patient at a dosage such that the 16 hour blood trough level is e.g. 0.1 to 20, e.g. 0.1 to 10, e.g. 1 to 10, preferably 3 to 6 µg per ml of MPA. IL-2 transcription inhibitors, e.g. cyclosporine may be delivered to a patient at a dosage such that the 16 hour blood trough level of, e.g. cyclosporine is e.g. up to 1500 ng per ml, e.g. 50 to 1500, e.g. 50 to 1000 ng per ml, e.g. up to 500 ng per ml, for example 50 to 500 ng per mi, more particularly 100 to 500 ng per ml, e.g. 300 to 500 ng per ml. Rapamycin and/or derivatives thereof, e.g. 40-O-(2-hydroxyethyl)-rapamycin may be delivered to a patient at a dosage such that the 16 hour blood trough level of, e.g. 40-O-(2-hydroxyethyl)-rapamycin is e.g. 1 to 90, e.g. 5 to 50, e.g. 10 to 35 ng per ml, more particu-larly 10 to 20 ng per ml.

The blood concentrations hereinabove described may be determined according to any convenient method known in the art. For example, blood may be collected in EDTA-coated containers, and detection of blood levels may be carried out by, e.g. radioimmunoassay or by ELISA. Detection of MPA is suitably carried out after protein precipitation using acetonitrile using an HPLC method with UV detection at 305 nm. From the data collected in this way, the blood trough levels may be calculated by methods known in the art.

Having regard to the blood trough levels stated hereinabove, the skilled person may determine those dosages that provide a therapeutic amount of compound at a level that is tolerated and which exhibits synergistic action in immune suppression.

The weight ratio of component compounds of the pharmaceutical compositions may vary having regard to the desired blood trough levels stated hereinabove.

Pharmaceutical compositions may comprise combinations of (a) an IL-2 transcription inhibitor and (b) an immunosuppressant compound or compounds that immunosuppress for B-cell-mediated or antibody-mediated rejection of xenografts in a weight ratio of e.g. about 1:50 to 1000:1, e.g. about 1:50 to 500:1, e.g. about 1:50 to 200:1, more particularly 1:2 to 50:1, e.g. 10:1. When more than one compound that immunosuppresses for B-cell-mediated or antibody-mediated rejection of xenografts is employed, for example in the case of a triple combination, the combined weight of said immunosuppressant compounds is reflected in the aforementioned weight ratio.

In a preferred embodiment a pharmaceutical composition comprises MPA sodium salt and cyclosporine in a weight ratio of e.g. about 1:0.03 to about 1:2, e.g. about 1:0.03 to about 1:0.5.

In another preferred embodiment a pharmaceutical composition comprises MPA sodium salt and 40-O-(2-hydroxyethyl)-rapamycin in a weight ratio of about 1:0.0005 to 0.015, to 1:0.001 to 0.0075, in particular, 1:0.0025.

In a particularly preferred pharmaceutical composition comprising the double combination of MPA sodium salt and cyclosporine, MPA sodium salt may be applied at a dosage of e.g. 10 to 200, e.g. 10 to 100 mg/kg/day, preferably 20 to 60 mg/kg/day, in particular 40 to 60 mg/kg/day; whereas cyclosporine may be applied at a dosage of e.g. 10 to 100, e.g. 10 to 50 mg/kg/day, preferably 10 to 15 mg/kg/day, in particular 3 to 6 mg/kg/day. Most preferably MPA sodium salt may be applied at a dosage of 20 mg/kg/day and cyclosporine may be applied at a dosage of 10 mg/kg/day.

In another particularly preferred pharmaceutical composition comprising a double combination of MPA sodium salt and 40-O-(2-hydroxyethyl)-rapamycin, MPA may be applied at dosages referred to in the preceding paragraph, whereas 40-O-(2-hydroxyethyl)-rapamycin may be applied at a dosage of from 0.05 to 1.5 mg/kg/day, e.g. 0.1 to 0.75 mg/kg/day, e.g. 0.25 to 0.5 mg/kg/day. Most preferably MPA sodium salt may be applied at a dosage of 20 mg/kg/day and 40-O-(2-hydroxyethyl)-rapamycin may be applied at a dosage of 1.5 mg/kg/day.

In yet another particularly preferred pharmaceutical composition comprising a double combination of cyclosporine and 40-O-(2-hydroxyethyl)-rapamycin, cyclosporine may be applied at a dosage of e.g. 10 to 100, e.g. 10 to 50 mg/kg/day, preferably 10 to 15 mg/kg/day, in particular 3 to 6 mg/kg/day; whereas 40-O-(2-hydroxyethyl)-rapamycin may be applied at a dosage of 0.05 to 1.5 mg/kg/day, e.g. 0.1 to 0.75 mg/kg/day, e.g. 025 to 0.5 mg/kg/day.

In yet another particularly preferred pharmaceutical composition comprising the triple combination aforementioned, MPA sodium salt may be applied at a dosage of e.g. 10 to 200, e.g. 10 to 100 mg/kg/day, preferably 20 to 60 mg/kg/day, in particular 40 to 60 mg/kg/day; cyclosporine may be applied at a dosage of e.g. 10 to 100, e.g. 10 to 50 mg/kg/day, preferably 10 to 15 mg/kg/day, in particular 3 to 6 mg/kg/day. 40-O-(2-hydroxyethyl)-rapamycin may be applied at a dosage of from 0.05 to 1.5 mg/kg/day, e.g. 0.1 to 0.75 mg/kg/day, e.g. 0.25 to 0.5 mg/kg/day. Most preferably MPA sodium salt may be applied at a dosage of 20 mg/kg/day, and 40-O-(2-hydroxyethyl)-rapamycin may be applied at a dosage of 1.5 mg/kg/day. Cyclosporine may be applied at a dosage of 10 mg/kg/day.

The dosages referred to hereinabove may be administered to a patient in any convenient way, for example individual dosages referred to hereinabove may be administered daily in 2 divided doses. Any regimen may be used, provided that therapeutic amounts of the individual compounds are delivered to the patient.

In larger mammals, for example humans, an indicated daily dosage for MPA sodium salt is in the range of 0.5 to 2.0 g/day, e.g. about 1.5 g/day, cyclosporine is in the range of from about 25 mg to about 1000 mg per day, preferably 50 mg to 500 mg per day, and 40-O-(2-hydroxyethyl)-rapamycin is in the range from about 0.25 mg to about 15 mg per day.

The application of the pharmaceutical composition may be preceded by the administration of a suitable induction therapy, chosen from any suitable induction therapy known in the art, for example a short course of cyclophosphamide, e.g. up to 40 mg/kg, e.g. 20 to 40 mg/kg i.v. per day for 4 days. Furthermore, a tapering course of steroids, e.g. methylprednisolone at a concentration of 1 mg/kg at day one tapering to a baseline of 0.2 mg/kg/day may be administered.

The compounds hereinabove described may be used in pharmaceutical compositions according to the invention in free or fixed combination, preferably in free combination. By 'free' is meant that each compound is formulated separately in a discrete dosage form. By 'fixed' is meant that the compounds are formulated together in one carrier. As a further embodiment, the pharmaceutical compositions may be both free and fixed whereby two or more compounds may be formulated in a single carrier whereas a further compound of the pharmaceutical composition may be formulated as a discrete dosage form.

Where one or more of the compounds are formulated separately, the individual dosage forms may be taken together or substantially at the same time (e.g. within fifteen minutes or less) so that, in the case of oral administration for example, said compounds are present simultaneously in the stomach.

The pharmaceutical composition according to the invention may be formulated in any convenient dosage form, the component compounds being either in a single carrier or formulated as discrete dosage forms as in a free combination, for example oral dosage forms, e.g. solid oral dosage forms or solutions or dispersions, or in forms suitable for intravenous administration.

Pharmaceutical compositions for oral administration of, e.g. cyclosporine and/or 40-O-(2-hydroxyethyl)-rapamycin, are suitably emulsions, microemulsions, preconcentrates of either, or solid dispersions, especially water-in-oil microemulsion preconcentrates or oil-in-water microemulsions.

Cyclosporine may be formulated in any of the ways known in the art, in particular the known microemulsion preconcentrate formulations of cyclosporine are particularly suitable for use in the present invention.

40-O-(2-hydroxyethyl)-rapamycin may be formulated in any of the ways known in the art, for example as a microemulsion (see WO 96/13273), as a fat emulsion for use in intravenous administration (see WO 97/25977), as a suspension (see WO 96/13239) or as a solid oral dosage form, for example, as a co-precipitate with a suitable carrier medium (a so-called solid dispersion) as more fully described in WO 97/03654 all of which documents are incorporated herein by reference.

MPA sodium salt may be formulated in any of the ways described in WO 97/38689 which is incorporated herein by reference, in particular as a solid oral dosage form, e.g. an enteric-coated tablet.

Pharmaceutical compositions according to the invention are useful as therapies in the treatment or prevention of xenograft rejection, including acute or chronic rejection of an organ from a discordant species, e.g. heart, lung, combined heart-lung, liver, kidney, islet cells, most especially when the rejection is mediated by B-cells or antibodies.

Whereas the pharmaceutical compositions are useful in the treatments as set forth in the preceding paragraph, nevertheless a significant obstacle in the successful treatment of patients with the afore-mentioned pharmaceutical compositions is the prevention or amelioration of hyperacute rejection.

Hyperacute rejection is the first immunological barrier to the transplantation of a donor organ from discordant species into humans. It occurs when the recipient's own immune system attacks and destroys the transplanted organ, usually within minutes or within a number of hours. Hyperacute rejection occurs in a xenograft because humans have preformed xenoreactive antibodies which bind to the animal tissue activating the human complement cascade and leading to graft damage. Accordingly, organ transplants from animal species, such as a pig, into humans may not be viable unless treatments are available that prevent hyperacute rejection.

Means for ameliorating hyperacute rejection are known in the art. For example, organs from pigs transgenic for human decay-accelerating factor (hDAF) may not be hyperacutely rejected upon transplantation into non-human primates. Similarly, extracorporeal removal of xenoantibodies from a recipient's blood is also known in the treatment of hyperacute rejection, see for example U.S. Pat. No. 5,817,528 or U.S. Pat. No. 5,651,968.

However, whereas hyperacute rejection may be prevented in this manner, antibodies may nevertheless trigger damage to the donor organ and thereby compromise the organ leading to poor early graft function or premature organ failure notwithstanding the administration of immunosuppressive therapies.

The applicant has now found that long term survival of a transgenic donor organ may be enhanced if a recipient receives treatment to remove xenoantibodies extracorporeally as well as receiving appropriate immunosuppressive drug therapy.

Accordingly, the invention provides in another aspect a method of treating a patient in need of such therapy comprising i) exposing the body fluid removed from a human recipient with a xenoantigenic material or anti human mono- or polyclonal antibodies or an other antibody adsorbent, which is bound to a biocompatible solid support, ii) reintroducing the treated body fluid into the recipient, and iii) treating the recipient with immunosuppressive drug therapy comprising a combination of immunosuppressant compounds selected from the group consisting of (a) IL-2 transcription inhibitor and (b) immunosuppressant compounds that immunosuppress for B-cell-mediated or antibody-mediated rejection of xenografts.

In another aspect, the group of immunosuppressant compounds consists of (a) an IL-2 transcription inhibitor and (b) immunosuppressant compounds that immunosuppress for B-cell-mediated or antibody-mediated rejection of xenografts.

Methods and materials for carrying out the steps i) and ii) referred to above are known in the art and suitable examples are described in U.S. Pat. No. 5,817,528 or U.S. Pat. No. 5,651,968, or published international application PCT EP98/02227 each of which are incorporated herein by reference.

In a particularly preferred aspect of the invention, the step i) may be carried out using an Ig-Therasorb® column thereby selectively immunoadsorbing IgM, IgG and IgA.

The step i) is usually carried out pre-operatively. However, alternatively or additionally it may be used perioperatively or post-operatively in parallel with the immunosuppressive drug therapy. Such post-operative use may be used if during treatment a build up of xenospecific antibodies is detected. Judicious use of the step i) and ii) pre-operatively, perioperatively and/or post-operatively in parallel with the immunosuppressive drug therapy may contribute significantly to the long term survival of donor organs.

In addition to the improvement of the early graft function, effective treatments need to inhibit T-cells and also B-cell-mediated or antibody-mediated rejection. Accordingly, preferred immunosuppressive drug therapies for use in step iii) comprise any of the pharmaceutical compositions, dosages and other aspects as hereinabove described.

There now follows a series of examples which are illustrative of the invention.

EXAMPLE 1

Organ Xenograft Studies: Porcine Kidney to Cynomolgus Monkey

Cynomolgus monkeys undergo heterotopic renal transplants using porcine kidneys transgenic for hDAF.

Immunosuppression consists of induction therapy consisting of cyclophosphamide, Neoral® and a tapering course of steroids followed by maintenance therapy with a free combination of cyclosporine and MPA sodium salt as set forth in Table 1.

Induction therapy consists of four non-consecutive daily intravenous injections of cyclophosphamide (40 mg/kg), Neoral® and methylprednisolone low dose treatment (1 mg/kg) day one and thereafter reducing the dose each day by 0.05 mg/kg, and subsequently to a baseline dose of 0.02 mg/kg/day as part of the maintenance therapy.

Maintenance therapy, subsequent to the induction therapy, consists of cyclosporine (Neoral®) and MPA sodium salt (MPA Na in Table 1) in the form of a powder in a 1% methylcellulose (Courtauld's Chemicals) solution.

Dosing occurs twice daily at 8 am and 4 pm and the doses set forth in Table 1 are equally divided for that purpose. Dosing is carried out by gastric gavage under slight ketamine anaesthesia (10 mg/kg) in a volume of 2 ml/kg of body weight followed by flushing with at least 10 ml/kg physiological saline.

TABLE 1

Tolerability of a combination of MPA Sodium and Cyclosporine in Cynomolgus Monkeys. (Dosages in mg/kg).

| MPA Na | Cyclosporine[2] | Outcome |
|---|---|---|
| 50 bid | 25 bid | Tolerated |
| 100 bid | 25 bid | Tolerated |
| 40 + 60[1] | 30 bid | Tolerated |

[1]First dose at 7 am, second at 3 pm
[2]NEORAL ®
bid = Twice per day

Significant prolongation of the xenografts treated with the foregoing combinations were observed compared with monotherapy of the individual compounds of the combinations.

EXAMPLE 2

Organ Xenograft Studies: Hamster-to-Rat

Donor male Chinese hamsters are obtained from Tongji Medical University.

Recipient male SD rats are obtained from Tongji Medical University.

Maintenance therapy consists of MPA sodium in the form of a powder in a 1% methylcellulose (Courtauld's Chemicals) solution, cyclosporine (Neoral®), and/or 40-O-(2-hydroxyethyl)-rapamycin in the form of a solid dispersion at 9.09% by weight, together with HPMC (81.82% by weight) and lactose (9.09% by weight).

All compounds are freshly prepared before administration and dissolved in distilled water. The compounds are administered daily per oral by gavage (<2 ml/kg body weight).

Anaesthesia is carried out using Hypnorm and Hypnovel Iv. anaesthesia.

TABLE 2 illustrates significant prolongation of xenografts using compositions according to the invention.

| Treatment Schedule (mg/kg/day) | Graft survival (days) | n |
|---|---|---|
| MPA Sodium salt (20) Cyclosporine A (10) | 5, 5, 6, 6, 6, 14 | 6 |
| MPA Sodium salt (20) 40-O-(2-hydroxyethyl)-rapamycin (1.5) | 6, 7, 7, 11, 16, 17 | 6 |
| MPA Sodium salt (20) 40-O-(2-hydroxyethyl)-rapamycin (1.5) Cyclosporine A (10) | 6, 7, 10, 10, 12 | 5 | n: number of patients

EXAMPLE 3

Use of Immunoadsorption in Heterotopic Xenotransplantation of hDAF Pig Hearts to Baboons Baboons undergo heterotopic heart transplants using porcine hearts transgenic for hDAF.

Materials for Immunosuppression are:—

Cyclosporin A (CyA): (Sandimmun®) given via intramuscular injection at a concentration of 100 mg/ml; and Optoral® given by oral gavage at 100 mg/ml.

Cyclophosphamide (CyP): Endoxan® for injection at 200 mg/ml

Mycophenolate sodium: In a form describe in Example 2 above.

Methylprednisolon (MPS): Urbason® in a 40 mg vial.

Prednisolon (PDN): Prednesol® as a 5 mg tablet.

Post-operative anesthesia is carried out using buprenorphine hydrochloride. Nausea and vomiting are treated using metoclopramide.

Animals are dosed twice a day with a 12 hour interval. Animals receive the following regimen: CyA is applied initially as i.m. injection at a dose of 25 mg/kg/day after surgery. On the first post-operative day 20 mg/kg is applied i.m. In the afternoon Optoral is given by oral gavage at a dose of 100 mg/kg. Thereafter doses are modified according to CyA trough levels aiming at >1500 ng/ml.

CyP is given i.v. on the day before surgery at 40 mg/kg, on the day of surgery at 20 mg/kg and on the second post-operative day at 20-30 mg/kg. An additional dose may be given up to 20 mg/kg on day 4. The last dose may be modified according to WBC and platelet count. Thereafter. CyP is administered only for rejection treatment.

Mycophenolic acid sodium is given orally twice a day to ensure trough levels of 3-6 µg/ml.

MPS is given at the time of surgery at a dose of 1 mg/kg i.v. On the following two days the same dose will be applied orally and thereafter the dose is reduced to 0.05 mg/kg/day until a baseline of 0.2 mg/kg is reached.

Body weight of the animals is taken during morning dosing. Food is provided one hour after morning dosing and water is freely available.

For Xenotransplantation of transgenic organs immunoadsorption is carried out pre-operatively using an Ig-Therasorb® column. According to the xenoreactive natural antibody titre; between 6 and 14 cycles are carried out withdrawing blood from a central venous catheter.

The treatment was well tolerated and the xenografts exhibited good long term survival.

The invention claimed is:

1. A method of suppressing the rejection and prolonging the survival of a xenograft from a pig transgenic for hDAF in a baboon or human recipient, the method comprising:
   administering to a baboon or human recipient of a porcine xenograft, pharmaceuticals comprising
      cyclosporine A,
      cyclophosphamide,
      a compound comprising mycophenolic acid, a pharmaceutically acceptable salt of mycophenolic acid, or a mycophenolic combination thereof, and
      a steroid comprising prednisolone, methylprednisolone, or a steroidal combination thereof;
   treating a bodily fluid of the baboon or human recipient extracorporeally to remove at least pre-formed xenoreactive antibodies using an immunoadsorbent column; and
   reintroducing the treated body fluid into the baboon or human recipient, thereby suppressing the rejection and promoting the survival of the porcine xenograft.

2. The method of claim 1, wherein the pharmaceuticals are administered in a pharmaceutical composition.

3. The method of claim 1, wherein at least two of the pharmaceuticals are administered together in a fixed combination.

4. The method of claim 1, wherein the pharmaceuticals are administered in free combination.

5. The method of claim 1, wherein the compound comprises the sodium salt of mycophenolic acid.

6. The method of claim 1, wherein the steroid comprises prednisolone and methylprednisolone.

7. The method of claim 1, wherein the treating is performed pre-operatively, peri-operatively, or post-operatively, or any combination thereof.

8. The method of claim 7, wherein the treating is performed pre-operatively and post-operatively.

9. The method of claim 7, wherein the treating is performed in parallel with the administering of pharmaceuticals.

10. The method of claim 1 wherein the treating is performed using an immunoadsorbent column that selectively adsorbs IgM, IgG, and IgA.

11. The method of claim 1, wherein the recipient is a baboon.

12. The method of claim 1, wherein the recipient is a human.

13. The method of claim 1, wherein the porcine xenograft comprises a pig heart.

14. The method of claim 1, wherein the porcine xenograft comprises a pig kidney.

15. The method of claim 1, wherein the porcine xenograft comprises a pig lung.

16. The method of claim 1, wherein the porcine xenograft comprises a pig liver.

17. The method of claim 1, wherein the porcine xenograft comprises pig islet cells.

18. A method of suppressing the rejection and prolonging the survival of a xenograft from a pig transgenic for hDAF in a human recipient, the method comprising:
   administering to the human recipient a pharmaceutical composition comprising
      cyclosporine A,
      cyclophosphamide,
      a sodium salt of mycophenolic acid,
      prednisolone, and
      methylprednisolone;
   treating bodily fluid of the human recipient extracorporeally to remove at least pre-formed xenoreactive antibodies using an immunoadsorbent column that selectively adsorbs IgM, IgG, and IgA; and reintroducing the treated body fluid into the human recipient;

wherein the treating and reintroducing steps are performed pre-operatively and post-operatively, thereby suppressing the rejection and promoting the survival of the porcine xenograft.

19. The method of claim 18, wherein the porcine xenograft comprises a pig heart.

20. The method of claim 18, wherein the porcine xenograft comprises a pig kidney.

* * * * *